US012636400B2

(12) United States Patent
Areskoug et al.

(10) Patent No.: US 12,636,400 B2
(45) Date of Patent: May 26, 2026

(54) POLYURETHANE FOAM FOR USE IN A WOUND PAD

(71) Applicant: Mölnlycke Health Care AB, Gothenburg (SE)

(72) Inventors: Stefan Areskoug, Sävedalen (SE); James W. Davis, Cumming, GA (US); William Laliberte, Wiscasset, ME (US); Eva Larkö Sander, Västra Frölunda (SE)

(73) Assignee: Mölnlycke Health Care AB, Mölndal (SE)

( * ) Notice: Subject to any disclaimer, the term of this patent is extended or adjusted under 35 U.S.C. 154(b) by 133 days.

(21) Appl. No.: 18/722,000

(22) PCT Filed: Dec. 1, 2022

(86) PCT No.: PCT/EP2022/084009

§ 371 (c)(1),
(2) Date: Jun. 20, 2024

(87) PCT Pub. No.: WO2023/117354

PCT Pub. Date: Jun. 29, 2023

(65) Prior Publication Data

US 2024/0415999 A1 Dec. 19, 2024

(30) Foreign Application Priority Data

Dec. 22, 2021 (EP) ..................................... 21216926

(51) Int. Cl.
*A61L 15/18* (2006.01)
*A61L 15/26* (2006.01)
(Continued)

(52) U.S. Cl.
CPC ............. *A61L 15/18* (2013.01); *A61L 15/425* (2013.01)

(58) Field of Classification Search
CPC ........ A61L 15/00; A61L 15/18; A61L 15/425; A61L 15/44; A61L 26/00; A61L 26/0066;
(Continued)

(56) References Cited

U.S. PATENT DOCUMENTS 5,849,805 A * 12/1998 Dyer ......................... C08F 2/32
521/64
8,263,100 B2 * 9/2012 Areskoug ............... A61L 15/46
521/905
(Continued)

FOREIGN PATENT DOCUMENTS

EP 3191039 7/2017
EP 3191144 7/2019
WO WO 2008/104276 9/2008

OTHER PUBLICATIONS

PMC, Polyurethane Foams: Past, Present, and Future, Sep. 27, 2018.*
(Continued)

*Primary Examiner* — Alireza Nia
*Assistant Examiner* — Andrew Jun-Wai Mok
(74) *Attorney, Agent, or Firm* — Ballard Spahr LLP

(57) ABSTRACT

Described is a polyurethane foam use as a wound pad or wound pad layer, wherein the polyurethane foam has an antimicrobial salt. Also described is a wound pad and a wound dressing that includes the polyurethane foam, a method for manufacturing a wound pad or wound pad layer and to a method for manufacturing a wound dressing.

9 Claims, 3 Drawing Sheets

(51) Int. Cl.
   *A61L 15/42* (2006.01)
   *A61L 15/46* (2006.01)

(58) Field of Classification Search
   CPC ............... A61L 2300/00; A61L 31/146; A61F
   2013/00634; A61F 2013/00089; A61F
   2013/00582; A61F 2013/00757; A61F
   2013/53925; A61F 5/443; A61F 13/00;
   A61F 13/00008; A61F 13/00021; A61F
   13/00063; A61F 13/00085; A61F
   13/0233; A61F 13/0243; A61F 13/0246;
   A61F 13/0253; A61K 9/70
   See application file for complete search history.

(56) References Cited

U.S. PATENT DOCUMENTS

| | | | | |
|---|---|---|---|---|
| 2017/0258956 A1* | 9/2017 | Flach | ....................... | A61L 15/44 |
| 2019/0223445 A1* | 7/2019 | Seo | ......................... | A01N 25/08 |

OTHER PUBLICATIONS

Flinn Scientific, Solubility Rules, Jul. 19, 2019.*
International Search Report and Written Opinion were mailed on Jan. 17, 2023 by the International Searching Authority for International Application No. PCT/EP2022/084009 filed on Dec. 1, 2022 and published as WO2023117354 (Applicant—Molnlycke Healthcare AB) (7 pages).

* cited by examiner

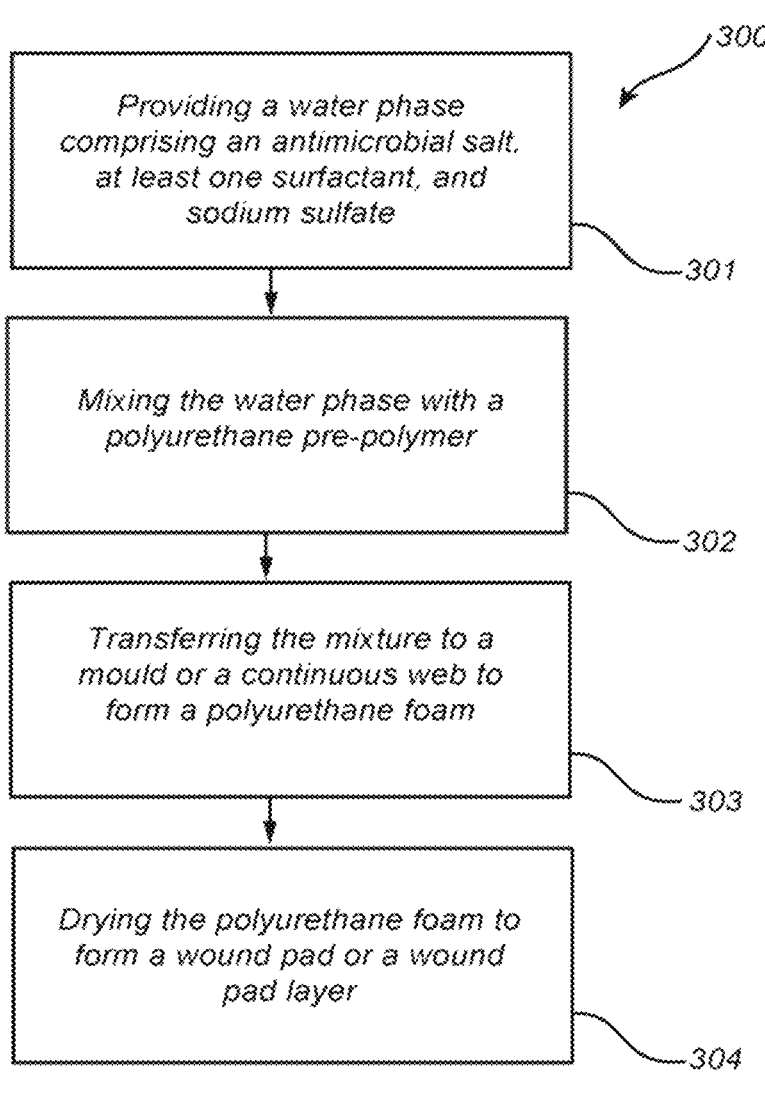
_300_
_Providing a water phase comprising an antimicrobial salt, at least one surfactant, and sodium sulfate_
_301_
_Mixing the water phase with a polyurethane pre-polymer_
_302_
_Transferring the mixture to a mould or a continuous web to form a polyurethane foam_
_303_
_Drying the polyurethane foam to form a wound pad or a wound pad layer_
_304_
_Fig. 3_

POLYURETHANE FOAM FOR USE IN A WOUND PAD

CROSS-REFERENCE TO RELATED APPLICATIONS

This application is a U.S. National Phase Application of International Application No. PCT/EP2022/084009, filed Dec. 1, 2022, which claims priority to European Application No. 21216926.2, filed Dec. 22, 2021, each of which are hereby incorporated by reference in their entirety.

TECHNICAL FIELD

The present disclosure generally relates to a polyurethane foam for use as a wound pad or wound pad layer, wherein the polyurethane foam comprises an antimicrobial salt. The present disclosure also relates to a wound pad and a wound dressing comprising the polyurethane foam, a method for manufacturing a wound pad or wound pad layer and to a method for manufacturing a wound dressing.

BACKGROUND

Infection is a common problem in chronic and surgical wounds. A surgical site or an open wound is a suitable environment for bacteria to accommodate and colonize. A bacterial infection in the wound or at the skin surrounding the wound may disrupt the normal wound healing process and result in chronic, non-healing wounds.

In wound treatment, antimicrobial agents are often used to eliminate or reduce the infection of the wound. To that end, various types of antimicrobial dressings have been developed. Examples of antimicrobial agents that have been explored for use in wound dressings include conventional antiseptics, antibiotics, antimicrobial peptides, or metallic agents with antimicrobial properties.

Antimicrobial agents may be provided as antimicrobial salts, wherein the positively charged cations of the salts, in contact with liquid, may bind to the negatively charged cell walls of bacteria and disrupt the cell walls.

Examples of antimicrobial salts include e.g. chlorhexidine salts and silver salts. Such antimicrobial salts may be incorporated into the dressing structure or provided as coatings on a skin-facing surface of the dressing. Dressings comprising silver salts in various forms are known from e.g. EP 3 191 039A1, EP 3 191 144B1 and WO 2008/104276.

While silver is a well-recognized antimicrobial in wound care, the use of silver is also associated with environmental concerns since silver is a heavy metal with toxic properties. Furthermore, silver is typically associated with high costs.

Another challenge with antimicrobial salts, particularly when incorporated into the dressing structure, e.g. into the wound pad of the dressing, is securing proper release of the antimicrobial from the dressing. Typically, high amounts of antimicrobial salts are required for accomplishing the release of a relatively small amount of the antimicrobial salt. Accordingly, a significant amount of the antimicrobial salt remains within the dressing structure, e.g. in the wound pad, and is not released therefrom.

In consideration of the environmental burden of a discarded dressing comprising significant amounts of antimicrobial agents, e.g. silver, an efficient use of the antimicrobial must be balanced against its antimicrobial activity.

In view of this, there is a need to alleviate the above-mentioned drawbacks and to provide an antimicrobial wound care product which allows for an improved release of the antimicrobial from the wound care product, and wherein the wound care product is cost-efficient and poses less demands on the environment.

SUMMARY

In view of the above mentioned problems, it is an object of the present disclosure to provide improvements with respect to providing an antimicrobial wound care product being less expensive to produce and which provides for an improved release of the antimicrobial agent.

According to a first aspect, there is provided a polyurethane foam for use as a wound pad or a wound pad layer, wherein the polyurethane foam comprises at least one antimicrobial salt, and wherein the polyurethane foam further comprises sodium sulfate.

The present disclosure is based on the realization that the incorporation of sodium sulfate into the polyurethane foam enhances the release of the antimicrobial cations present in the foam. Without wishing to be bound by theory, it is believed that sodium sulfate acts as a "catalyst" and promotes the release of the antimicrobial cations from the polyurethane foam. The inventors have surprisingly found that even when the amount of antimicrobial salt is significantly reduced in the polyurethane foam, an enhanced release of antimicrobial is observed when the salt is combined with sodium sulfate.

Accordingly, a polyurethane foam of the present disclosure provides an improved release of antimicrobial to the wound site. The amount of the active agent; i.e. the antimicrobial salt present in the polyurethane foam may thus be considerably reduced and yet yield the same or even improved results. Consequently, a polyurethane foam according to the present disclosure is considered as being both environmentally sound and cost efficient.

Furthermore, the incorporation of sodium sulfate yields a softer, more conformable and more drapable foam structure.

Also, sodium is a simple, non-toxic and common cation, and sodium sulfate is regarded as a non-expensive compound.

In exemplary embodiments, the solubility of the sodium sulfate is higher than the solubility of the antimicrobial salt.

Accordingly, the sodium sulfate dissolves faster than the antimicrobial salt in contact with liquid, e.g. blood or other body fluids. The higher solubility of the sodium sulfate may trigger the release of positively charged cations from the polyurethane foam.

The antimicrobial salt may be any salt that can inhibit and/or kill bacteria or other microorganisms commonly encountered in an infected wound.

For example, the antimicrobial salt may be a silver salt, a chlorhexidine salt or a polyhexamethylene biguanide (PHMB) salt.

In exemplary embodiments, the antimicrobial salt is a silver salt.

With silver containing wound pads, there is typically a delicate balance between the desire to utilize as low amounts of silver as possible in the wound pad (due to environmental concerns) but amounts high enough to trigger the release of silver from the wound pad. Releasing silver from the wound pad is a challenge. Accordingly, the polyurethane foam of the present disclosure is greatly favored by the incorporation of sodium sulfate when a silver salt is utilized as the antimicrobial salt.

If the silver is not released from the polyurethane foam, which forms a wound pad or a wound pad layer, silver may remain in the wound dressing structure, such that the remaining bound silver will be wasted and discarded before the silver ions have been released.

The sodium sulfate of the polyurethane foam promotes the release of silver ions at a consistent level throughout the duration of use and secures an efficient utilization of the antimicrobial silver.

The silver salt may be any pharmaceutically acceptable silver salt that remains stable during sterilization of the wound pad or wound dressing incorporating the wound pad.

For example, the silver salt may be silver sulfate, silver citrate, silver acetate, silver carbonate, silver lactate and silver phosphate, or a mixture of such salts.

In contact with liquid; i.e. blood or body fluids exuded by a wound, positively charged silver ions are released to the wound surface, which can promote wound healing and prevent infection at the wound site.

Preferably, the silver salt is silver sulfate.

Silver sulfate can kill a wide range of microorganisms commonly present in an infected wound. Furthermore, an improved release of silver is observed when the silver salt is silver sulfate.

In embodiments, the amount of silver in the polyurethane foam is from 0.4 to 2.4% by weight, preferably from 0.7 to 1.5% by weight.

This range is beneficial to secure sufficient killing of infectious bacteria at the wound site. Furthermore, this range secures that the wound pad or wound pad layer will release a significant proportion of silver during use of the wound dressing and prevents unnecessary amounts of silver remaining in the wound pad or wound pad layer, when discarded.

In embodiments, the amount of sodium sulfate in the polyurethane foam is from 0.2 to 3.0% by weight, preferably from 0.6 to 2.0% by weight.

These ranges are beneficial to promote the release of the antimicrobial agent; i.e. the antimicrobial cations.

Furthermore, the incorporation of sodium sulfate in an amount of from 0.2 to 3.0% by weight, preferably from 0.6 to 2.0% by weight yields a foam being soft, conformable and drapable. If too much sodium sulfate is incorporated in the polyurethane foam, the properties of the foam may be impaired. The pores of the polyurethane foam may become denser and more compacted, which may impair the fluid handling capacity of the wound pad. This is particularly the case when the polyurethane foam is incorporated in a wound dressing, and an adhesive skin contact layer is coated directly onto the polyurethane foam forming the wound pad or wound pad layer.

According to a second aspect, there is provided a wound pad comprising a polyurethane foam as described hereinbefore.

The wound pad may consist of the polyurethane foam as described hereinbefore. Alternatively, the wound pad may comprise a wound pad layer comprising the polyurethane foam and one or more additional pad-forming layer(s). For example, the wound pad may comprise a liquid spreading or distribution layer, one or more absorbent layers, e.g. one or more superabsorbent layer(s) etc.

According to a third aspect, there is provided a wound dressing comprising a backing layer, an adhesive skin contact layer and a wound pad as described hereinbefore, wherein the wound pad is arranged between the backing layer and the adhesive skin contact layer.

The features of the first aspect apply mutatis mutandis to the second and third aspects of the present disclosure.

In exemplary embodiments, the adhesive skin contact layer comprises a second antimicrobial compound, wherein the second antimicrobial compound is integrated in the adhesive skin contact layer and/or is provided as a coating on the adhesive skin contact layer.

The second antimicrobial compound may be an antimicrobial salt or any other compound having an antimicrobial effect. Accordingly, the antimicrobial effect can be boosted and tailored to meet the demands of a variety of wounds. For example, the release of the second antimicrobial compound from the adhesive skin contact layer may be slower or quicker than the release of the antimicrobial salt from the wound pad depending on the specific wound care situation.

According to a fourth aspect, there is provided a method for manufacturing a wound pad or wound pad layer comprising:

a) providing a water phase comprising an antimicrobial salt and at least one surfactant;

b) mixing the water phase with a polyurethane prepolymer, c) transferring the mixture obtained in step b) to a mould or a continuous web to form a polyurethane foam; and d) drying the polyurethane foam to form a wound pad or wound pad layer, wherein the water phase in step a) further comprises sodium sulfate.

The foam obtained by the method is a hydrophilic polyurethane foam. The hydrophilic polyurethane foam is porous and comprises a plurality of pores, capable of handling large amounts of liquid.

In exemplary embodiments, the polyurethane prepolymer is an isocyanate-terminated polyether having a functionality of more than 2.

In exemplary embodiments, the antimicrobial salt is a silver salt, preferably silver sulfate.

According to a fifth aspect, there is provided a method for manufacturing a wound dressing comprising:

providing a wound pad comprising a polyurethane foam as described hereinbefore or manufactured as described hereinbefore, wherein the wound pad has a first, skin-facing surface and a second, opposing surface, applying an adhesive skin contact layer to the first, skin-facing surface of the wound pad applying a backing layer to the second, opposing surface of the wound pad.

According to a sixth aspect, there is provided the use of sodium sulfate to promote the release of silver from a wound pad comprising a polyurethane foam and at least one silver salt, preferably silver sulfate.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF DRAWINGS

The various aspects of the present disclosure, including its particular features and advantages, will be readily understood from the following detailed description and the accompanying drawings, in which:

FIG. 3 schematically outlines the steps of forming a wound pad or wound pad layer according to the method of the present disclosure.

DETAILED DESCRIPTION

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person.

Figure 1:
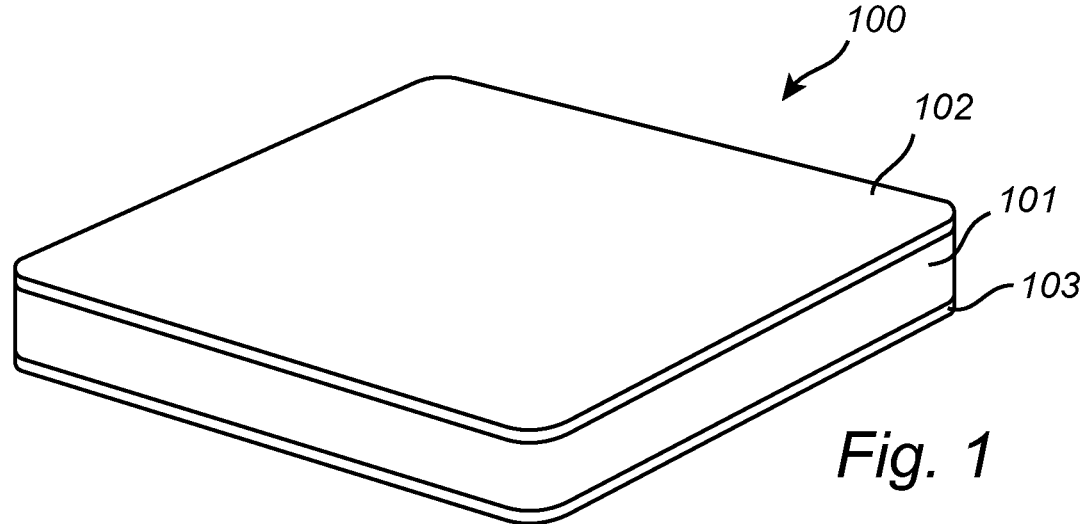
FIG. 1 illustrates a schematic perspective view of a wound dressing comprising a polyurethane foam according to an exemplary embodiment of the present disclosure.

With reference to FIG. 1, a wound dressing 100 is conceptually illustrated. The wound dressing 100 comprises a polyurethane foam. The polyurethane foam comprises at least one antimicrobial salt, wherein the polyurethane foam further comprises sodium sulfate.

The polyurethane foam is preferably a hydrophilic polyurethane foam. Accordingly, the hydrophilic polyurethane foam is also absorbent. An infected wound typically exudes large amounts of exudate, and the wound pad must be capable of properly handling such exudate.

The polyurethane foam is porous and may comprise pores having an average pore size in the range of from 30 and 1000 μm.

The antimicrobial salt may be any salt that can prevent and/or kill bacteria or other microorganisms commonly encountered in an infected wound.

For example, the antimicrobial salt may be selected from a silver salt, a chlorhexidine salt or a polyhexamethylene biguanide (PHMB) salt.

In exemplary embodiments, the antimicrobial salt is a silver salt.

Examples of suitable silver salts include silver sulfate, silver citrate, silver acetate, silver carbonate, silver lactate and silver phosphate or a mixture of these salts.

Sodium sulfate is particularly useful in conjunction with a silver salt due to the well known challenges of securing release of silver from the dressing, as well as the demands posed on the environment utilizing silver.

The concentration of the antimicrobial salt in the polyurethane foam may be from 0.2 to 2.5 mg/cm$^2$, e.g. from 0.4 to 1.4 mg/cm$^2$.

If the antimicrobial salt is a silver salt, the amount of silver in the polyurethane foam may be from 0.4 to 2.4% by weight, e.g. from 0.6 to 1.8% by weight, e.g. from 0.7 to 1.5% by weight.

As mentioned hereinbefore, this range is suitable for securing an antimicrobial effect and for providing an appropriate balance between a sufficient release of antimicrobial (e.g. silver) while also preventing unnecessary amounts of antimicrobial (e.g. silver) remaining in the wound pad when discarded.

In embodiments, the amount of sodium sulfate in the polyurethane foam is from 0.2 to 3.0% by weight, e.g. from 0.6 to 2.0% by weight.

The concentration of sodium sulfate in the polyurethane foam may be from 0.1 to 1.0 mg/cm$^2$, preferably from 0.2 to 0.7 mg/cm$^2$.

These ranges are beneficial to trigger the release of the antimicrobial, even when the antimicrobial is present in low amounts in the polyurethane foam.

Furthermore, the foam is soft and conformable and has an optimized liquid handling.

To trigger release of silver ions, the solubility of the sodium sulfate is preferably higher than the solubility of the antimicrobial salt.

The "solubility" refers to the solubility in water. The solubility may be measured at 25° C.

The sodium sulfate dissolves faster than the antimicrobial salt in contact with liquid, e.g. blood or other body fluids. The higher solubility of the sodium sulfate may trigger the release of positively charged cations from the polyurethane foam.

For example, the solubility of the sodium sulfate may be at least 8 times, e.g. at least 15 times, e.g. at least 30 times higher than the solubility of the antimicrobial salt, measured in water at a temperature of 25° C.

The dressing 100 schematically illustrated in FIG. 1 comprises a backing layer 102, an adhesive skin contact layer 103 and a wound pad 101 comprising the polyurethane foam as described herein before, wherein the wound pad 101 is arranged between the backing layer and the adhesive skin contact layer.

The wound pad 101 has an first, skin-facing surface facing the adhesive skin contact layer 103 and a second, opposing surface facing the backing layer 102.

In the embodiment illustrated in FIG. 1, the wound pad 101 consists of the polyurethane foam as described hereinbefore. It is, however, conceivable that the wound pad comprises one or more additional pad-forming layer(s). For example, the wound pad may comprise one or more wound pad layers comprising the polyurethane foam.

The thickness of the wound pad or wound pad layer comprising the polyurethane foam may be from 2 to 10 mm, e.g. from 3 to 6 mm, measured in dry conditions.

In the embodiment illustrated in FIG. 1, the wound pad is co-extensive with the backing layer 102 and the adhesive skin contact layer 103. Accordingly, the wound pad has the same surface area as the backing layer 102 and the adhesive skin contact layer.

The backing layer 102 is the outermost layer of the dressing. The backing layer may e.g. comprise polyurethane, polyethylene or polypropylene. Typically, the backing layer comprises a polyurethane film. For example, the backing layer may comprise a polyurethane film having a thickness of from 10 μm to 50 μm, e.g. from 15 to 30 μm. The backing layer 102 may be partly or fully attached to the wound pad, e.g. by means of an adhesive or by heat lamination. In the embodiment illustrated in FIG. 1, the backing layer is typically heat laminated onto the wound pad 101

The adhesive skin contact layer 103 is configured to detachably adhere the dressing to a dermal surface. In other words, the adhesive skin contact layer 103 is configured to contact the skin or the wound of a wearer.

The adhesive skin contact layer may comprise a silicone based adhesive, e.g. a silicone gel coating. A silicone based adhesive is gentle to the skin and allows for a non-traumatic removal of the dressing from the skin or the wound of a patient. The silicone based adhesive skin contact layer may comprise one or more sub-layers When the polyurethane foam is the wound pad layer in contact with the underlying adhesive skin contact layer, the adhesive skin contact layer is typically provided as a coating on the second (bottom) surface of the wound pad.

Figure 2:
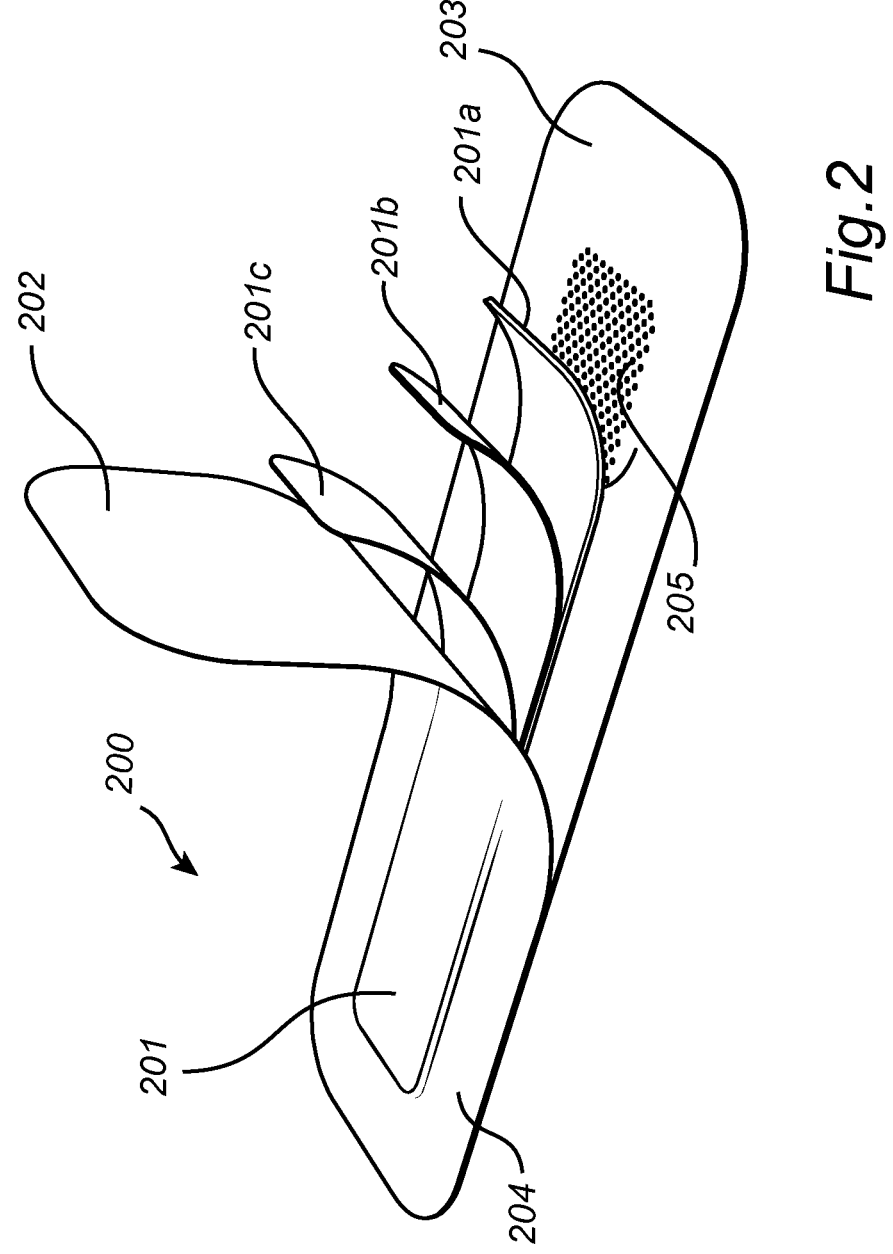
FIG. 2 illustrates a schematic perspective view of a wound dressing according to another exemplary embodiment of the present disclosure.

In FIG. 2, a so called "bordered wound dressing" is illustrated. The wound dressing 200 comprises a backing layer 202, an adhesive skin contact layer 203 and a wound pad 201 arranged between the backing layer 202 and the adhesive skin contact layer 203. The backing layer 202 and the adhesive skin contact layer 203 are configured to extend beyond the contour of the wound pad 201 to form a border portion 204.

In the wound dressing 200 illustrated in FIG. 2, the wound pad 201 has a surface area that is smaller than the surface area of the backing layer 202 and the adhesive skin contact layer 203.

The wound pad 201 may, as illustrated in FIG. 2 comprise more than one pad-forming layers. In exemplary embodiments, the wound pad comprises two or more layers having different properties. The pad-forming layers may be laminated or adhesively attached.

For example, the wound pad may comprise the polyurethane foam as described hereinbefore and a superabsorbent layer and/or a liquid distribution layer.

The wound pad illustrated in FIG. 2 comprises a first absorbent layer 201*a*, a liquid distributing layer 201*b* and a second absorbent layer 201*c*.

The polyurethane foam as described hereinbefore may form the first 201*a* and/or the second 201*b* absorbent layer of the wound pad.

In exemplary embodiments, the first absorbent layer 201*a* is a foam layer comprising the polyurethane foam.

The second absorbent layer 201*c* may be a superabsorbent layer; i.e. a layer comprising a superabsorbent material. The superabsorbent layer has the capacity to absorb large amounts of wound exudate. The superabsorbent material may be in the form of particles, fibers, flakes or similar. For example, the superabsorbent material may comprise superabsorbent polymers (SAP) or superabsorbent fibers (SAF).

The liquid distributing layer 201*b* may comprise any material having the ability to distribute the exudate in an efficient manner. For example, the liquid distributing layer 201*b* may comprise a nonwoven material. A nonwoven imparts an appropriately balanced rigidity to the layer and to the dressing as such. It may also efficiently distribute and spread liquid absorbed by the first absorbent layer, e.g. the polyurethane foam, such that it can be evaporated through the backing layer 202 over a large surface. For example, the nonwoven may comprise viscose, polyester or blends thereof.

The wound pad layers 201*a-c* can be joined by adhesion, lamination, using e.g. pressure and heat.

The wound pad construction illustrated in FIG. 2 and described hereinbefore prevents accumulation of body liquids close to the skin, and improves the liquid handling of the dressing. Most wounds will contain some exudate, but the level of exudate may vary. In a chronic wound, the exudate production may be very large due to the ongoing inflammation. A wound dressing having the construction as explained above is suited for handling large amounts of exudate, and prevents maceration of the skin surrounding the wound.

The wound dressing is not limited to the construction illustrated in FIG. 2.

For example, the absorbent pad may comprise additional layers, such as liquid transport layers, various combinations of foam and nonwoven layers laminated together.

The backing layer 202 of the wound dressing illustrated in FIG. 2 may be the same as the backing layer 102 of the wound dressing illustrated in FIG. 1; i.e. it may comprise polyurethane, polyethylene or polypropylene. In the embodiment illustrated in FIG. 2, the backing layer is typically adhesively attached to the adhesive skin contact layer 203. The backing layer 202 may be fully or partially adhesively attached to the wound pad 201.

The adhesive skin contact layer 203 may be similar to the adhesive skin contact layer described with reference the adhesive skin contact layer 103 in FIG. 1; i.e. it may comprise a silicone based adhesive.

The adhesive skin contact layer of the wound dressing 200 of FIG. 2 typically comprises a silicone based adhesive and a sub-layer. The sub-layer may be a polymeric film, and the silicone based adhesive may be coated onto the polymeric film.

Accordingly, the adhesive skin contact layer 203 may be a laminate comprising at least one polymeric film and an adhesive silicone gel layer.

The polymeric film simplifies the manufacturing process, and provides stability and integrity to the silicone based skin contact layer.

The polymeric film is preferably a breathable film and may comprise e.g. polyethylene, polyamide, polyester or polyurethane. Preferably, the polymeric film comprises polyurethane. The thickness of the polyurethane film may be from 15 to 100 μm, e.g. from 20 to 80 μm, preferably from 20 to 60 μm.

Examples of suitable silicone gels for use in the adhesive skin contact layer (103, 203) include the two component RTV systems, such as SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive skin contact layer is typically at least 20 μm. The thickness of the adhesive skin contact layer may be from 50 to 200 μm.

In exemplary embodiments, the adhesive skin contact layer comprises a plurality of perforations 205.

The perforations 205 improve the transfer of wound exudate into the dressing. The perforations 205 typically extend through the polymeric film and the silicone gel coating.

In FIG. 2, the adhesive skin contact layer 203 comprises a plurality of perforations 205 in the area underlying the absorbent pad 201 but is void of perforations in the area forming the border portion 204. The lack of perforations in the border portion of the dressing is beneficial to improve the adhesion at the border portion 204 of the dressing and thereby improve the stay-on ability of the dressing.

It is beneficial to have an even distribution of adhesive over the surface of the pad 201 in order to keep the dressing in place during use.

In exemplary embodiments, the adhesive skin contact layer (103, 203) may comprise a second antimicrobial compound, wherein the second antimicrobial compound is integrated in the adhesive skin contact layer and/or is provided as a coating on the adhesive skin contact layer.

The second antimicrobial compound may be an antimicrobial salt as described hereinbefore or a different antimicrobial compound.

When the second antimicrobial compound is provided as an antimicrobial coating, the coating may be a continuous or discontinuous coating on the adhesive skin contact layer. For example, spray coating may be used to apply such an antimicrobial coating. The antimicrobial coating comprising the second antimicrobial compound is typically provided on the non-perforated parts of the adhesive skin contact layer 203. The antimicrobial coating may be soluble in an aqueous medium. Accordingly, the coating dissolves in contact with wound exudate such that a relatively quick antimicrobial effect can be realized.

It is also conceivable, in embodiments where the wound pad comprises a plurality of pad-forming layers, to incorporate an additional antimicrobial compound into one or more of such pad-forming layers.

The second antimicrobial compound of the adhesive skin contact layer improves the antimicrobial effect of the dressing.

According to another aspect, and with reference to FIG. 3, a method for manufacturing a wound pad or a wound pad layer is schematically outlined. The method comprises:

a) providing a water phase comprising an antimicrobial salt and at least one surfactant (step 301)

b) mixing the water phase with a polyurethane prepolymer (step 302), c) transferring the mixture obtained in step b) to a mould or a continuous web to form a polyurethane foam (step 303), and d) drying the polyurethane foam to form a wound pad or a wound pad layer (step 304), wherein the water phase in step a) further comprises sodium sulfate.

The method of the present disclosure allows for the sodium sulfate and the antimicrobial salt to be distributed substantially homogenously in the polyurethane foam. This way, the antimicrobial salt becomes integrated into the foam and bound within the cell walls of the foam. The resulting polyurethane foam is hydrophilic and absorbent and capable of handling large amounts of wound exudate.

In step a), a part of the antimicrobial salt may be dissolved in the water phase and a part may be dispersed in the water phase.

The surfactant utilized is typically a non-ionic surfactant. The surfactant improves the water-wicking properties of the polyurethane foam. For example, the non-ionic surfactant may be an oxypropylene-oxyethylene block copolymer.

The polyurethane pre-polymer is typically hydrophilic.

In exemplary embodiments, the polyurethane pre-polymer is an isocyanate-terminated polyether, preferably with a functionality of more than 2. For example, a diisocyanate-terminated polyether may be used.

The diisocyanate-terminated polyethers may be based on hexamethylene diisocyanate (HDI), toluene diisocyanate (TDI) or methylene diphenyl diisocyanate (MDI).

During the reaction between the water and the polyurethane prepolymer, carbon dioxide is formed as a by-product. Carbon dioxide may act as a blowing agent in the foaming process.

Furthermore, amines may be generated during the reaction, which may act as catalysts during the foaming process.

The reaction mixture is subsequently transferred to a mould or a continuous web, whereby a polyurethane foam is obtained (step 303).

The mould or web may be lined with a casting paper before the mixture is added. The casting paper may be removed before the drying step.

During this step (step 303), the reaction mixture is cured and the polymerization reaction is terminated. The casting paper may then be removed.

The polyurethane foam is then dried (step 304). The step of drying is not limited to a particular drying method. For example, the polyurethane foam may be heated, e.g. to a temperature of about 100 to 150° C. during at least 5 minutes. The polyurethane foam is preferably dried to a moisture content of at most 10% (wt), preferably at most 8% (wt), most preferably at most 5% (wt).

The polyurethane foam forming the wound pad or wound pad layer may then be rolled on plastic cores with a paper in-between the layers and packaged before incorporation in a wound dressing. The wound pad may be cut into shape by techniques known in the art.

As mentioned hereinbefore, the antimicrobial salt is preferably a silver salt, e.g. silver sulfate.

The water phase of step a) may comprise from 0.3 to 4.0% by weight, e.g. from 0.5 to 2.5% by weight, e.g. from 0.7 to 2.0% by weight of the antimicrobial salt.

If the antimicrobial salt is a silver salt, e.g. silver sulfate, the water phase of step a) may comprise from 0.2 to 3.0% by weight, e.g. from 0.5 to 2.5% by weight, e.g. from 0.7 to 2.0% by weight of silver sulfate.

Even small amounts of the antimicrobial salt can be utilized to yield and improved release of antimicrobial from the final foam structure The water phase may comprise from 0.1 to 3.0% by weight, e.g. 0.3 to 2.5% by weight, e.g. from 0.4 to 2.0% by weight, e.g. from 0.6 to 1.6% by weight of sodium sulfate.

Even small amounts of sodium sulfate in the water phase can promote and trigger the release of antimicrobial from the foam structure.

The inventors have found that the above specified ranges are suitable for providing an improved release of antimicrobial, e.g. silver, from the final wound pad comprising the polyurethane foam.

The polyurethane prepolymer may be added to the water phase in a dispensing and mixing equipment, e.g. in an amount of from 30 to 60% by weight.

According to another aspect, there is provided a method for manufacturing a wound dressing 100 comprising:

providing a wound pad 101 comprising a polyurethane foam as described hereinbefore or manufactured as described hereinbefore, wherein the wound pad has a first, skin-facing surface and a second, opposing surface, applying an adhesive skin contact layer 103 to the first, skin-facing surface of the wound pad applying a backing layer 102 to the second, opposing surface of the wound pad.

The backing layer forms the top layer of the wound dressing. The adhesive skin contact layer forms the bottom layer of the wound dressing.

As mentioned hereinbefore, the wound pad may comprise one or more wound pad layers comprising the polyurethane foam. Alternatively, or additionally, the wound pad may comprise additional pad-forming layers.

The additional pad-forming layers, where present, may attached to the wound pad layer comprising the polyurethane foam by any means, e.g. by adhesion or lamination.

The backing layer may be adhesively attached to the wound pad. Alternatively, the backing layer may be heat laminated onto the wound pad.

The adhesive skin contact layer may be coated onto the wound pad by techniques well known in the art. Alternatively, the adhesive skin contact layer comprises an adhesive coating (e.g. a silicone gel coating) on a polymeric film. In such embodiments, the adhesive skin contact layer is typically adhesively attached to the wound pad.

According to another aspect, the present disclosure relates to the use of sodium sulfate to promote the release of silver from a wound pad comprising a polyurethane foam and at least one silver salt, preferably silver sulfate.

Examples

Five silver containing polyurethane foam samples, with different levels of sodium sulfate ranging from 0-1.2%, were evaluated. The thickness of the polyurethane foam layer was about 5 mm. In each of the samples tested, the amount of silver was 0.8% by weight.

To determine the silver release in a silver containing polyurethane foam, the foams were punched into samples having a diameter of 31 mm. 2 ml of Simulated Wound Fluid (SWF) was added to the samples, which were then incubated at 35° C.±2 and 90% RH for 24 hours. The liquid was squeezed out by placing the sample in disposable syringe and 100 ul of this liquid was collected in centrifuge tubes for silver analysis.

The silver amount in the SWF was determined using inductively coupled plasma-optical emission spectroscopy (ICP-OES) in axial mode. A matrix-matched calibration curve was constructed as a five-point calibration curve in the concentrations of 1, 7, 50, 300 and 2000 mg/l, where the levels were based on the sample volume of 100 µl. Both the calibration curve, the blank and the samples were diluted with a solution of hydrochloric acid and nitric acid in order to dissolve any bound silver. Yttrium was added as internal standard (IS).

The results are illustrated in table 1 below, which show that the addition of sodium sulfate yielded an increase in silver release from the wound dressings.

TABLE 1

| Amount of silver released from the wound dressing | |
| --- | --- |
| % by weight sodium sulfate in the polyurethane foam | Released silver (mg/l) |
| 0 | 95 |
| 0.65 | 104 |
| 1.3 | 134 |
| 1.95 | 173 |

In addition, a polyurethane foam, identical in construction as the samples described hereinbefore was used as a reference. The only difference was that this sample contained 2.5% by weight of silver. The amount of released silver was 83 mg/l for this sample.

These results clearly demonstrate that the incorporation of sodium sulfate significantly enhances the release of silver from the polyurethane foam.

Terms, definitions and embodiments of all aspects of the present disclosure apply mutatis mutandis to the other aspects of the present disclosure.

Even though the present disclosure has been described with reference to specific exemplifying embodiments thereof, many different alterations, modifications and the like will become apparent for those skilled in the art.

Variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A polyurethane foam for use as a wound pad or a wound pad layer, wherein said polyurethane foam comprises at least one silver salt, wherein an amount of silver salt in said polyurethane foam consists of from 0.4 to 2.4% by weight, wherein said polyurethane foam further comprises sodium sulfate, wherein an amount of sodium sulfate in said polyurethane foam consists of from 0.2 to 3.0% by weight, wherein the sodium sulfate enhances the release of the at least one silver salt in the polyurethane foam during use of the wound pad or the wound pad layer.

2. A wound pad comprising the polyurethane foam according to claim 1.

3. A wound dressing comprising a backing layer, an adhesive skin contact layer and the wound pad according to claim 2, wherein said wound pad is arranged between said backing layer and said adhesive skin contact layer.

4. The wound dressing according to claim 3, wherein said adhesive skin contact layer comprises a second antimicrobial compound, wherein said second antimicrobial compound is integrated in said adhesive skin contact layer and/or is provided as a coating on said adhesive skin contact layer.

5. The polyurethane foam according to claim 1, wherein a solubility of said sodium sulfate is higher than solubility of said at least one silver.

6. The polyurethane foam according to claim 1, wherein said at least one silver salt is silver sulfate.

7. A method for manufacturing a wound dressing comprising:

providing a wound pad comprising the polyurethane foam according to claim 1, wherein said wound pad has a first, skin-facing surface and a second, opposing surface, applying an adhesive skin contact layer to said first, skin-facing surface of said wound pad, applying a backing layer to said second, opposing surface of said wound pad.

8. A method for manufacturing a wound pad or wound pad layer comprising: a) providing a water phase comprising at least one silver salt and at least one surfactant, b) mixing the water phase with a polyurethane pre-polymer, c) transferring the mixture obtained in step b) to a mould or a continuous web to form a polyurethane foam; and d) drying the polyurethane foam to form a wound pad or wound pad layer, wherein an amount of silver salt in said dried polyurethane foam consists of from 0.4 to 2.4% by weight, wherein an amount of sodium sulfate in said dried polyurethane foam consists of from 0.2 to 3.0% by weight, characterized in that said water phase in said step a) further comprises sodium sulfate such that the sodium sulfate enhances the release of the at least one silver salt in the formed polyurethane foam during use of the wound pad or the wound pad layer.

9. The method according to claim 8, wherein said polyurethane polymer is an isocyanate-terminated polyether having a functionality of more than 2.

* * * * *